United States Patent [19]

Bauer et al.

[11] Patent Number: 5,531,987
[45] Date of Patent: Jul. 2, 1996

[54] METHOD FOR EXTRACTING MALODOROUS COMPOUNDS PRESENT IN A FORMULATION CONTAINING AT LEAST ONE COMPOUND CARRYING A THIOL GROUP AND DEODORIZED COMPOSITIONS THUS OBTAINED

[75] Inventors: Daniel Bauer, Le Raincy; Françoise Richard, Montreuil sous Bois; Muriel Hassoun, Villepinte; Gérard Malle, Villiers sur Morin; Henri Samain, Bievres, all of France

[73] Assignee: L'Oreal, Paris, France

[21] Appl. No.: 285,541

[22] Filed: Aug. 2, 1994

[30] Foreign Application Priority Data

Aug. 2, 1993 [FR] France ................ 93 09486

[51] Int. Cl.$^6$ .................... A61L 9/01; A61K 7/11
[52] U.S. Cl. ............... 424/76.21; 424/70.5; 424/70.51
[58] Field of Search ............... 424/76.21, 70.5, 424/70.51

[56] References Cited

U.S. PATENT DOCUMENTS 4,749,732  6/1988  Kohl et al. .................. 424/70.51

FOREIGN PATENT DOCUMENTS

0261387B1  5/1991  European Pat. Off..
2675046   10/1992  France.
9301791    2/1993  WIPO.

OTHER PUBLICATIONS

Patent Abstracts of Japan, vol. 4, No. 101 (C19) Jul. 19, 1980.

*Primary Examiner*—Thurman K. Page
*Assistant Examiner*—Pamela S. Webber
*Attorney, Agent, or Firm*—Cushman Darby & Cushman

[57] ABSTRACT

Method for extracting malodorous compounds present in a liquid formulation containing at least one compound bearing a thiol functional group of formula:

$$HS-A-Y-B \quad (I)$$

in which said formulation is placed in contact with a pulverulent absorbing agent, in order to obtain a deodorized composition, intended for a subsequent use, said absorbing agent being such that, when it is suspended in an aqueous solution containing 92 g/l of thioglycolic acid, said aqueous solution also contains at least 30% by weight of the initial thioglycolic acid after contact for 15 minutes.

15 Claims, No Drawings

METHOD FOR EXTRACTING MALODOROUS COMPOUNDS PRESENT IN A FORMULATION CONTAINING AT LEAST ONE COMPOUND CARRYING A THIOL GROUP AND DEODORIZED COMPOSITIONS THUS OBTAINED

The present invention relates to a method of extraction of the malodorous compounds present in a formulation containing at least one compound bearing a thiol (—SH) functional group and to the deodorized compositions, in particular cosmetic compositions, obtained by this method.

Organic compounds bearing thiol functional group(s) are well-known compounds which have an ever-increasing number of applications. One of these applications is the permanent reshaping (curling and straightening) of hair which consists, in a first phase, in opening the disulfide (S—S) bonds of the cystine units of keratin using a composition containing at least one organic compound bearing a thiol functional group which acts as a reducing agent (reduction step), thereby enabling the desired shape to be imparted to the hair; then, after having rinsed the hair, in reconstituting, in a second phase, said disulfide bonds by applying an oxidizing composition to the hair (oxidation step, also known as the fixing step), in order to fix the hair in the shape which it has been given; with this aim, thioglycolic acid, thiolactic acid or mixtures thereof, or alternatively the esters of these acids, for example the monothioglycolates of glycerol or of glycol, or also cysteine or cysteamine, are particularly used. Thioglycolic or thiolactic acids and salts thereof are also used in depilatory milks and creams. Thioglycolic and thiolactic acids, as well as cysteine, are also employed as intermediate products in the manufacture of pharmaceutical products.

Unfortunately, although compounds bearing a thiol functional group generally have, in the pure state, an odor which is not unpleasant, they always contain, in practice, sulfur-containing compounds such as hydrogen sulfide and low-molecular-weight mercaptans, in particular methanethiol or ethanethiol, which have a particularly unpleasant, nauseating odor. Very low amounts of these sulfur-containing compounds are sufficient for their presence to be detected by smell, the nose being, in this case, the best detection instrument. In the following decription and in the claims, these sulfur-containing compounds will be denoted by the term "malodorous compounds".

The presence of these malodorous compounds is linked to various poorly-understood processes for the decomposition of compounds bearing a thiol group, in particular by oxidation.

In the various applications of the compounds bearing a thiol functional group, and more particularly in their cosmetic applications, the odor released by the products used constitutes a genuine nuisance for the users. It has been attempted to mask the odor with perfumes, but the odor is generally too powerful to be able to be masked significantly.

It has thus been sought to remove the malodorous compounds. With this aim, it has already been proposed, in Japanese Patent Application published as No. 84-027 866, to deodorize thioglycolic acid, pure or in aqueous solution, by extraction using a $C_4$-$C_8$ non-aromatic hydrocarbon. Given that, in order to carry out the extraction, it is necessary to use a relatively large installation, it is practically impossible to deodorize the compounds bearing a thiol functional group just before their use, so that their storage is, in practice, obligatory. Now, it has been observed that, although this method makes it possible to obtain a deodorized acid, the deodorization effect obtained is not long-lasting because the malodorous compounds reform during storage, in particular in the presence of oxygen, and, in certain cases, the odor even returns at a higher level than initially.

A method for purifying thioglycolic acid has been described in Japanese Patent Application JP-A-55 064 569; this method is intended to remove two manufacturing by-products, namely dithioglycolic acid (HOOC—$CH_2$—S—S—$CH_2$—COOH) and thiodiglycolic acid (S—($CH_2$—$CO_2H)_2$), which contain no —SH groups but S—S and S—C bonds respectively: the two by-products are absorbed while the thioglycolic acid remains in the solution. This document thus did not make it possible to separate, on the one hand, a compound bearing —SH groups such as thioglycolic acid and, on the other, malodorous compounds generally consisting of mercaptans which also bear —SH groups.

A method was thus desired which makes it possible, just before use, for the malodorous compounds to be removed from formulations containing at least one compound bearing a thiol functional group without it being necessary to use a large installation.

It is known, moreover, to decontaminate gaseous or dissolved compositions, in particular to remove $H_2S$ and low-molecular-weight mercaptans, by physical absorption on a pulverulent absorbent product. However, it is well known that these absorbent products are most often charged with oxygen. A person skilled in the art thus had every reason to think that by placing these absorbent products in contact with compounds bearing a thiol functional group, the degradation of these compounds by oxygenation with formation of malodorous compounds would be too rapid, so that it would be impossible, even for a limited period, to obtain a deodorized composition or to conserve the properties, in particular the reducing properties, of this composition.

According to the present invention, it has been found that in reality, contrary to the predisposition of the person skilled in the art, it was possible to use a pulverulent absorbing agent which was insoluble in the formulation containing at least one compound bearing a thiol functional group in order to deodorize efficiently said formulation, without the properties of the compound bearing a thiol group being significantly degraded.

The subject of the present invention is a method for extracting malodorous compounds present in a liquid formulation containing at least one compound carrying a thiol functional group of formula:

$$HS—A—Y—B \qquad (I)$$

in which formula Y represents —COO— or —NH— and
a) when Y denotes —COO—:
   A represents:
     the divalent radical: —$(CH_2)_n$ where n is 1 or 2
     the divalent radical:

where R represents a linear or branched $C_1$-$C_3$ alkyl radical, and
B represents the radicals —H; —$CH_2$—$CH_2OH$; —$CH_2$—CHOH—$CH_2OH$,

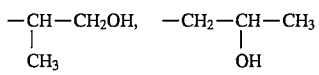

b) when Y represents —NH—

A represents

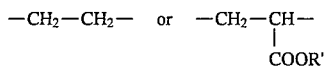

R' representing a methyl or ethyl radical

B represents —H or, when A represents —CH$_2$—CH$_2$—,

B also represents a radical —CO—R",

R" representing a linear or branched C$_1$–C$_4$ alkyl radical, and which comprises placing said formulation in contact, before its use, with a pulverulent absorbing agent which is insoluble in said formulation, said absorbing agent being such that, when it is suspended in an aqueous solution containing 92 g/l of thioglycolic acid, said aqueous solution also contains at least 30% by weight of the initial thioglycolic acid after contact for 15 minutes.

The liquid formulation subjected to the method according to the invention may contain a pure compound of formula (I) or a mixture of pure compounds of formula (I), when this (these) compound(s) is (are) available in liquid form, or alternatively a solution containing at least one compound of formula (I), it being possible for the compound(s) of formula (I) to be optionally combined with various formulation ingredients, depending upon their use. In addition, the liquid formulation may be provided in the form of a cream of greater or lesser thickness or of a gel of greater or lesser rigidity.

The compound(s) of formula (I) is (are) advantageously chosen from the group formed by thioglycolic (or mercaptoacetic) acid, thiolactic acid (or 2-mercaptopropionic acid), 3-mercaptopropionic acid, glyceryl monothioglycolate, glyceryl 2-mercaptopropionate, an azeotropic mixture of 2-hydroxypropyl thioglycolate and 2-hydroxy-1-methylethyl thioglycolate (as described in FR-A-2, 679, 448), cysteamine (or 2-aminoethanethiol) and the N-acyl derivatives thereof, the acyl radical containing from 2 to 5 carbon atoms, cysteine and methyl and ethyl cysteinates. Thioglycolic and thiolactic acids are preferred.

The absorbing agent preferably contains at least one absorbent product chosen from the group formed by:

activated charcoals, such as those marketed under the names "PICACTIF CB 506®", "PGV 120 EWN®", "PMC 2®" by the company "PICA", those marketed under the name "ACTICARBONE®" by the "C.E.C.A." and those marketed under the names "NORIT CA 1®", "NORIT CN 1®," "NORIT SA 2®," "NORIT SA 4®", "NORIT SX 2®", "NORIT SX ULTRA®" and "NORIT W 20®" by the company "NORIT", animal charcoal, talc, calcium carbonate, diatomaceous earth or clays, such as bentonites and montmorillonites, wood sawdust and absorbent organic polymers, such as the polymer obtained by polymerization of 2,6-diphenyl-para-oxyphenylene marketed under the name "TENAX®" by the company "INTERCHIM".

The absorbing agent preferably has a particle size between 0.1 and 100 µm.

The absorbing agent and the liquid formulation are placed in contact a short time before use, so that the reducing capacity of the formulation is sufficiently conserved, but nevertheless long enough before use for the malodorous compounds to have the time to be absorbed; it is preferable for the placing in contact to occur between 5 minutes and 30 minutes before use.

According to a first embodiment of the invention, the absorbing agent is mixed with the liquid formulation. It should be noted that, according to this embodiment, the composition consisting of the mixture containing the formulation and the absorbing agent is preferably used directly. With this aim, the formulation and the absorbing agent may be packaged separately and the mixing may be carried out only a short time before use of the composition.

According to a second embodiment, the liquid formulation is passed through a layer of absorbing agent: with this aim, it is possible, for example, to use the device described in FR-A-2,597,443 and to use thereafter the deodorized composition obtained.

Another subject of the present invention is the deodorized composition obtained by the method described above.

More particularly, the subject of the present invention is a composition of this type containing, on the one hand, a formulation which includes at least one compound of formula (I) and, on the other hand, a pulverulent absorbing agent mixed with said formulation: this composition is intended to be applied to a human keratinous substance such as the skin, head hair and body hair; this composition is preferably a cosmetic composition for the reshaping of hair or a depilatory composition.

The compound(s) of formula (I) is (are) generally present at a concentration between 2 and 30%, and preferably between 5 and 25%, by weight relative to the total weight of the composition and the absorbing agent is present at a concentration between 0.5 and 30% by weight relative to the total weight of the composition and preferably between 1 and 10% by weight relative to the total weight of the composition.

The pH of the composition is preferably between 5 and 12.5 and is obtained using a basifying agent such as, for example, aqueous ammonia, monoethanolamine, diethanolamine, triethanolamine, an alkali metal or ammonium carbonate or bicarbonate, or an alkali metal hydroxide, or using an acidifying agent such as, for example, hydrochloric acid, acetic acid, lactic acid, oxalic acid or boric acid. When the composition is intended to be used for the permanent reshaping of hair, the pH is generally between 5 and 10 and when it is intended to be used for hair removal, the pH is generally between 9 and 12.5.

The composition may additionally contain various formulation ingredients such as, for example, cationic polymers such as those used in the compositions of French Patents No. 79-32078 and No. 80-26421 or alternatively cationic polymers of ionene type such as those used in the compositions of French Patent No. 82-17364, softening agents such as quaternary ammonium derivatives of lanolin, protein hydrolysates, waxes, opacifying agents, perfumes, dyes, nonionic or cationic surface-active agents, alcohols such as ethanol, propanol, isopropanol, 1,2-propanediol, 1,2-butanediol or glycerol, treating agents or alternatively penetration agents, such as urea, pyrrolidone or thiamorpholinone.

The vehicle for the compositions according to the invention is preferably water or an aqueous-alcoholic solution of a lower alcohol such as ethanol, isopropanol or butanol.

It should be pointed out that the invention defined above was in no way suggested by Japanese Patent Application JP-A-55 064,569 mentioned previously. Indeed, it was not obvious, in view of this document, that all the compounds bearing —SH groups would not be bound to the absorbing agent, and that it would consequently be possible to separate thioglycolic acid and the other compounds of formula HS—A—YB from the malodorous compounds. According to the present invention, a cosmetic composition is prepared containing both thioglycolic acid and an absorbing agent, this composition being totally odorless. Notwithstanding, this result is obtained only with absorbing agents corresponding to a specific definition which is in no way suggested by the abovementioned Japanese patent application.

When the compositions are intended for a hair straightening or decurling operation, the reducing composition is preferably in the form of a cream., in order to keep the hair as straight as possible. These creams are produced in the form of emulsions, for example based on glyceryl stearate, glycol stearate, self-emulsifiable waxes, fatty alcohols, and the like. It is also possible to use liquids or gels containing thickening agents such as carboxyvinyl polymers or copolymers, which keep the hair in the smooth position during the exposure time.

In order to carry out the permanent reshaping of the hair, in a first step, the disulfide linkages of keratin are reduced by application, for approximately 5 to 60 minutes, of a composition defined above and then, in a second step, said linkages are reformed by application of an oxidizing composition or possibly by allowing atmospheric oxygen to act.

In order to wave the hair, a composition as defined above is applied to the wet hair which has been wound beforehand on rollers having a diameter of 4 to 20 mm, it being possible for the composition optionally to be applied while the hair is being wound; the reducing composition is subsequently left to act for a time of 5 to 60 minutes, preferably of 5 to 30 minutes, followed by thorough rinsing; after this, a fixing agent is applied to the wound hair, which agent allows the disulfide linkages of keratin to reform, for an exposure time of between 2 and 10 minutes. After removing the rollers, the hair is rinsed thoroughly. The fixing agent commonly used contains as oxidizing agent hydrogen peroxide, an alkali metal bromate, a persalt, a polythionate or a mixture of alkali metal bromate and persalt. The pH of the fixing agent is generally between 2 and 10. This oxidation may be carried out immediately or may be delayed.

In order to straighten or decurl the hair, a composition according to the invention is applied to the hair and the hair is then subjected to a mechanical reshaping which allows it to be fixed in its new shape, by an operation of smoothing the hair with a large-toothed comb, with the back of a comb or by hand. After an exposure time of 5 to 60 minutes, in particular of 5 to 30 minutes, a further smoothing is then performed, followed by careful rinsing and application of a fixing agent as defined above, which is allowed to act for approximately 2 to 10 minutes, and the hair is then rinsed thoroughly.

The examples below, given as a guide and with no limitation whatsoever being implied, will allow a better understanding of the invention.

EXAMPLE 1

I—Preparation

A—A reducing formulation is prepared, consisting of a 1M thioglycolic acid solution, the pH of which is adjusted to a value of 8.5 by addition of monoethanolamine. 20% by weight (relative to the weight of said formulation) of active charcoal marketed under the name "PICACTIF CB 506®" by the company "PICA" is subsequently added to the formulation obtained. A composition A is thus obtained, which is used, as indicated below, ten minutes after its preparation.

B—By way of comparison, a composition B, which is identical except that no activated charcoal is added, was also prepared, and it is also used ten minutes after its preparation.

II—Test

A permanent waving was carried out on two locks of identical natural hair the compositions A and B. Compositions A and B were used in an amount of 2 g of composition per 1 g of hair. They are applied to wet hair which has been wound beforehand on rollers. After an exposure time of 15 minutes, the hair was rinsed and then fixed with an 8 volumes hydrogen peroxide solution having a pH of 3, applied for 5 minutes, in an amount of 2 g per gram of hair, then rinsed again and dried.

It was observed that the curling obtained with the composition A is identical to that obtained with the composition B. Consequently, the presence of activated charcoal in the composition does not modify the reducing power of thioglycolic acid.

Furthermore, during the phase of reduction by the composition A, no disagreeable odor was detected; furthermore, after rinsing and fixing, no unpleasant odors were noticed. In contrast, with the composition B, the development of unpleasant odors was observed during the reduction phase.

EXAMPLE 2

I—Preparation

C—A 1M cysteamine solution was prepared and its pH was adjusted to a value of 8.5 by addition of monoethanolamine. 30% by weight (relative to the weight of the formulation) of activated charcoal marketed under the name "PM C2®" by the company "PICA" was added to this formulation. A composition C was obtained, which is used ten minutes after its preparation.

D—By way of comparison, a solution D which is identical to the composition C but which contains no activated charcoal was prepared simultaneously and is also used ten minutes after its preparation.

II—Test

A permanent waving was carried out with these two compositions C and D, in the same way as in Example 1, on natural dark-brown hair.

It was observed that, in both cases, the curling obtained was identical and that, in the case of the composition C, no unpleasant odors were formed during the reduction phase, whereas unpleasant odors were formed in the case of the composition D.

EXAMPLE 3

I—Preparation

E—A 1M cysteine solution was prepared and its pH was adjusted to a value of 8.5 by addition of monoethanolamine. 15% by weight (relative to the weight of the formulation) of a 50/50 mixture by weight of montmorillonite and activated charcoal, marketed under the name "FGV 120 EWN" by the company "PICA", was added to this formulation. A composition E is obtained which is used, as indicated below, ten minutes after its preparation.

F—By way of comparison, a composition F, which is identical to the composition E except that it contains neither clay nor activated charcoal, was prepared and is also used ten minutes after its preparation.

II—Test

A permanent waving was carried out on natural dark-brown hair using the compositions E and F and under the same conditions as in Example 1.

It was observed that the curling obtained with the composition E is identical to that obtained with the composition F and that, in the reduction phase of the permanent waving, no unpleasant odors were formed with the composition E, whereas unpleasant odors appeared with the composition F.

We claim:

1. A method for extracting a malodorous compound present in a liquid formulation containing a compound bearing a thiol functional group and having the formula $$HS-A-Y-B \quad (I)$$

wherein

Y represents —COO— or —NH— and (a) when Y represents —COO—,
A represents —$(CH_2)_n$— wherein n is 1 or 2 or $$-\underset{R}{\overset{|}{CH}}-$$

wherein R represents linear or branched $C_1$–$C_3$ alkyl, and B represents —H, —$CH_2$—$CH_2OH$, —$CH_2$—$CHOH$—$CH_2OH$, $$-\underset{CH_3}{\overset{|}{CH}}-CH_2OH \quad \text{or} \quad -CH_2-\underset{OH}{\overset{|}{CH}}-CH_3,$$

or (b) when Y represents —NH—,
A represents $$-CH_2-CH_2- \quad \text{or} \quad -CH_2-\underset{COOR'}{\overset{|}{CH}}-$$

wherein R' represents methyl or ethyl, and
B represents —H or, when A represents —$CH_2$—$CH_2$—, B also represents —CO—R" wherein R" represents linear or branched $C_1$–$C_4$ alkyl, the method comprising placing the liquid formulation in contact with a pulverulent absorbing agent to obtain a deodorized composition, the pulverulent absorbing agent being insoluble in the liquid formulation and, when suspended in an aqueous solution containing 92 g/l of thioglycolic acid, the aqueous solution also contains at least 30 percent by weight of initial thioglycolic acid after contact for 15 minutes.

2. The method of claim 1 wherein the compound of formula (I) is selected from the group consisting of thioglycolic acid, thiolactic acid, 3-mercaptopropionic acid, glyceryl monothioglycolate, glyceryl 2-mercaptopropionate, an azeotropic mixture of 2-hydroxypropyl thioglycolate and 2-hydroxy-1-methylethyl thioglycolate, cysteamine, and N-acyl cysteamine wherein said acyl moiety contains 2 to 5 carbon atoms, cysteine, methyl cysteinate and ethyl cysteinate.

3. The method of claim 1 wherein the pulverulent absorbing agent is selected from the group consisting of an activated charcoal, an animal charcoal, talc, calcium carbonate, diatomaceous earth, clay, wood sawdust and an absorbent organic polymer.

4. The method of claim 1 wherein the pulverulent absorbing agent has a particle size ranging from 0.1 to 100 μm.

5. The method of claim 1 wherein the liquid formulation and said pulverulent absorbing agent are placed in contact by mixing.

6. The method of claim 5 wherein the liquid formulation is placed in contact with said pulverulent absorbing agent at a time ranging from 5 to 30 minutes prior to the use of said deodorized composition.

7. The method of claim 1 wherein the liquid formulation is passed through a layer of the pulverulent absorbing agent.

8. A deodorized cosmetic composition for application to a human keratinous substance, the composition comprising (i) a compound having the formula $$HS-A-Y-B \quad (I)$$

wherein

Y represents —COO— or —NH— and (a) when Y represents —COO—,
A represents —$(CH_2)_n$— wherein n is 1 or 2 or $$-\underset{R}{\overset{|}{CH}}-$$

wherein R represents linear or branched $C_1$–$C_3$ alkyl, and B represents —H, —$CH_2$—$CH_2OH$, —$CH_2$—$CHOH$—$CH_2OH$, $$-\underset{CH_3}{\overset{|}{CH}}-CH_2OH, \quad -CH_2-\underset{OH}{\overset{|}{CH}}-CH_3$$

or (b) when Y represents —NH—,
A represents $$-CH_2-CH_2- \quad \text{or} \quad -CH_2-\underset{COOR'}{\overset{|}{CH}}-$$

wherein R' represents methyl or ethyl, and

B represents —H or, when A represents —$CH_2$—$CH_2$—, B also represents —CO—R" wherein R" represents linear or branched $C_1$–$C_4$ alkyl, and (ii) a pulverulent absorbing agent which is insoluble in said compound (i) and being selected from the group consisting of an activated charcoal, an activated charcoal with clay, animal charcoal, talc, calcium carbonate, diatomaceous earth, wood sawdust and an absorbent organic polymer.

9. The deodorized cosmetic composition of claim 8 wherein the compound of formula (I) is present in an amount ranging from 2 to 30 percent by weight based on the total weight of the composition and the pulverulent absorbing agent is present in an amount ranging from 0.5 to 30 percent by weight based on the total weight of said composition.

10. The deodorized cosmetic composition of claim 8 wherein said compound of formula (I) is present in an amount ranging from 5 to 25 percent by weight based on the total weight of the composition and the pulverulent absorbing agent is present in an amount ranging from 1 to 10 percent by weight based on the total weight of said composition.

11. The deodorized cosmetic composition of claim 8 having a pH ranging from 5 to 12.5.

12. The deodorized cosmetic composition of claim 11 containing in an amount effective to adjust the pH thereof, (a) a basifying agent selected from the group consisting of aqueous ammonia, monoethanolamine, diethanolamine, triethanolamine, alkali metal carbonate, alkali metal bicarbonate, ammonium carbonate, ammonium bicarbonate and alkali metal hydroxide, or (b) an acidifying agent selected from the group consisting of hydrochloric acid, acetic acid, lactic acid, oxalic acid and boric acid.

13. The deodorized cosmetic composition of claim 11 having a pH ranging from 5 to 10.

14. The deodorized cosmetic composition of claim 11 having a pH ranging from 9 to 12.5.

15. The deodorized cosmetic composition of claim 8 wherein said compound of formula (I) is present as an aqueous or aqueous-alcoholic solution.

* * * * *